United States Patent
Boldingh

(10) Patent No.: US 7,230,152 B1
(45) Date of Patent: Jun. 12, 2007

(54) PROCESS FOR SELECTIVE AROMATICS DISPROPORTIONATION WITH INCREASED CONVERSION

(75) Inventor: Edwin P. Boldingh, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 717 days.

(21) Appl. No.: 10/736,013

(22) Filed: Dec. 15, 2003

(51) Int. Cl.
*C07C 5/52* (2006.01)

(52) U.S. Cl. .................. 585/470; 585/475; 585/906

(58) Field of Classification Search ........... 585/475, 585/470, 906
See application file for complete search history.

(56) References Cited

U.S. PATENT DOCUMENTS

| | | | |
|---|---|---|---|
| 4,016,219 A | 4/1977 | Kaeding | 260/672 T |
| 4,097,543 A | 6/1978 | Haag et al. | 260/672 T |
| 4,182,923 A | 1/1980 | Chu | 585/475 |
| 4,629,717 A | 12/1986 | Chao | 502/208 |
| 6,114,592 A | 9/2000 | Gajda et al. | 585/475 |
| 6,191,331 B1 | 2/2001 | Boldingh | 585/475 |
| 6,359,185 B1 | 3/2002 | Boldingh et al. | 585/475 |
| 6,429,347 B1 | 8/2002 | Boldingh | 585/475 |

*Primary Examiner*—Thuan Dinh Dang
(74) *Attorney, Agent, or Firm*—James C Paschall; David J. Piasecki

(57) ABSTRACT

An improved process is disclosed for the selective disproportionation of toluene. The process preferably uses a disproportionation catalyst comprising a pentasil type zeolite such as MFI that is bound with aluminum-phosphate. Running the process at a toluene conversion greater than about 30 wt-% and at a hydrogen-to-hydrocarbon ratio less than 3.0, and especially a ratio of 0.1 to 1.0, improves the maximum yield of para-xylene. Optional periodic rejuvenation by increasing the hydrogen-to-hydrocarbon ratio removes some carbon deposits and restores catalyst activity. An inert diluent gas assists in selective pre-coking of the catalyst as well.

7 Claims, 2 Drawing Sheets

US 7,230,152 B1

PROCESS FOR SELECTIVE AROMATICS DISPROPORTIONATION WITH INCREASED CONVERSION

FIELD OF THE INVENTION

This invention relates to an improved process for the conversion of aromatic hydrocarbons, such as conversion of toluene into para-xylene. More specifically, the present invention concerns selectivation and operation of a disproportionation process at low levels of hydrogen to permit favorable coke formation and aromatics conversion.

BACKGROUND OF THE INVENTION

The xylene isomers are produced in large volumes from petroleum as feedstocks for a variety of important industrial chemicals. The most important of the xylene isomers is para-xylene, the principal feedstock for polyester which continues to enjoy a high growth rate from large base demand. Ortho-xylene is used to produce phthalic anhydride, which has high-volume but mature markets. Meta-xylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene is selectively disproportionated to yield benzene and $C_8$ aromatics from which the individual xylene isomers are recovered.

A current objective of many petrochemical and aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene thus is a favorable objective, and processes to convert toluene have been commercialized to obtain high xylene yields.

U.S. Pat. No. 4,016,219 discloses a process for toluene disproportionation using a catalyst comprising a zeolite which has been modified by the addition of phosphorus in an amount of at least 0.5 mass-%. The crystals of the zeolite are contacted with a phosphorus compound to effect reaction of the zeolite and phosphorus compound. The modified zeolite then may be incorporated into indicated matrix materials. U.S. Pat. No. 4,097,543 discloses toluene disproportionation for the selective production of para-xylene using a zeolite which has undergone controlled pre-coking. The zeolite may be ion-exchanged with a variety of elements from Group IB to VIII, and composited with a variety of clays and other porous matrix materials.

U.S. Pat. No. 4,182,923 discloses a process for toluene disproportionation with a high conversion of the toluene to benzene and para-xylene by use of an aluminosilicate zeolite of silica to alumina ratio above 12 and which has been modified by treatment with ammonium hydrogen phosphate to deposit phosphorus. U.S. Pat. No. 4,629,717 discloses a phosphorus-modified alumina hydrogel formed by gelation of a homogeneous hydrosol. The composite has a relatively high surface area of 140 to 450 $m^2/g$ and high activity and selectivity in 1-heptene conversion tests.

U.S. Pat. No. 6,114,592 discloses an improved process combination for the selective disproportionation of toluene. The combination comprises selective hydrogenation of a toluene feedstock followed by a zeolitic catalyst. U.S. Pat. No. 6,359,185 discloses an oil-dropped zeolitic catalyst in an amorphous aluminum phosphate binder that enhances selectivity.

U.S. Pat. No. 6,191,331 discloses a pre-coking method that avoids a large temperature rise by using a low pressure in the presence of nitrogen and a low ratio of hydrogen-to-hydrocarbon. U.S. Pat. No. 6,429,347 discloses that running a process at a hydrogen-to-hydrocarbon ratio between 0.2 and 0.5 improves the selectivity of para-xylene and decreases the selectivity of benzene.

Workers in the field of aromatics disproportionation continue to seek processes and catalysts having exceptionally high conversion to para-xylene from toluene combined with favorable selectivity and stability.

SUMMARY OF THE INVENTION

It is an object of the present invention to provide an improved process for the disproportionation of aromatic hydrocarbons. A specific objective is to obtain a maximally high yield of xylenes by selective toluene disproportionation.

This invention is based on the unexpected finding that operation at low levels of hydrogen-to-hydrocarbon promotes increased yields of para-xylene by permitting operation at higher conversion of toluene than used previously. Low levels of hydrogen also improve the selective pre-coking and conditioning of zeolitic catalysts when combined with a nitrogen diluent prior to use in the high conversion process.

The present invention is directed to a process for the production of xylene comprising a selective disproportionation zone at conditions comprising a toluene conversion level greater than 30 wt-% and hydrogen-to-hydrocarbon ratio less than 3, preferably less than 1. In the disproportionation zone the stream is contacted with a disproportionation catalyst at disproportionation conditions. The disproportionation catalyst preferably comprises a pentasil zeolitic aluminosilicate, most preferably NMF. This catalyst is subjected to a pre-coking step prior to its use in the disproportionation zone in order to increase its selectivity to para-xylene in the product beyond its equilibrium concentration.

These as well as other objects and embodiments will become apparent from the detailed description of the invention.

DESCRIPTION OF THE PREFERRED EMBODIMENTS

Figure 1:
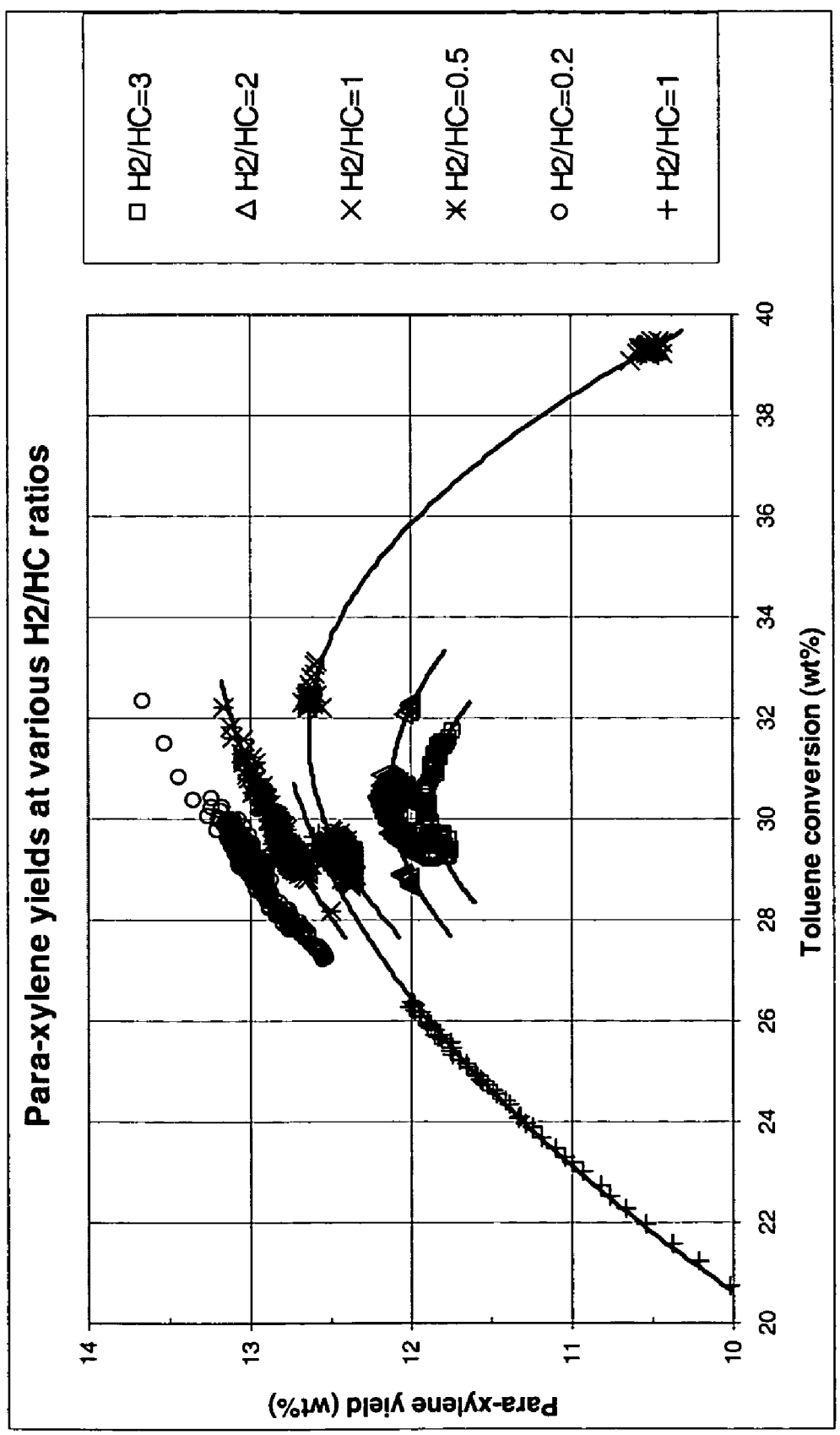
FIG. 1 shows the yields of para-xylene at various hydrogen-to-hydrocarbon ratios as toluene conversion increases over a selectively pre-coked catalyst.

A broad embodiment of the present invention is a selective toluene disproportionation process operating at low hydrogen-to-hydrocarbon ratio for increased selectivity to para-xylene. Accordingly, one necessary element of the process is a zeolitic catalyst which has been subjected to a pre-coking step, prior to its use for disproportionation, in order to deposit a controlled concentration of carbon on the catalyst and increase para-xylene selectivity. The para-xylene content of the para-xylene-rich product from disproportionation of the present invention is in excess of its equilibrium concentration at disproportionation conditions.

The selective disproportionation process zone of the present invention comprises a molecular sieve and a refractory inorganic oxide. The preferred molecular sieves are zeolitic aluminosilicates, or zeolites, which may be any of those which have a $SiO_2/Al_2O_3$ ratio greater than about 10, preferably greater than 20, and a pore diameter of about 5 to 8 Angstroms (Å). Specific examples of zeolites which can be used are the MFI, MEL, EUO, FER, MFS, MTT, MTW, TON, MOR and FAU types of zeolites. Pentasil zeolites MFI, MEL, MTW and TON are preferred, and MFI-type zeolite, often designated ZSM-5, is especially preferred.

The preparation of the preferred MFI-type zeolite is well known in the art. The zeolite preferably is prepared by crystallizing a mixture containing an alumina source, a silica source, an alkali metal source, water and an alkyl ammonium compound or its precursor.

A refractory binder or matrix is utilized to facilitate fabrication of the disproportionation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphorus oxide, zinc oxide and silica. Alumina and/or silica are preferred binders. The amount of zeolite present in the bound catalyst can vary considerably but usually is present in an amount from about 30 to 90 mass-% and preferably from about 50 to 80 mass-% of the catalyst.

A preferred binder or matrix component is a phosphorus-containing alumina (hereinafter referred to as aluminum phosphate) component. The phosphorus may be composited with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/zeolite/phosphorus compound into particles by employing an oil-drop method as described herein below and calcining the spherical particles.

The preferred oil-drop method of preparing the aluminum phosphate is described in U.S. Pat. No. 4,629,717 which is incorporated by reference. The technique described in the '717 patent involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is then added to the sol. Preferred phosphorus compounds are phosphoric acid, phosphorous acid and ammonium phosphate. The relative amount of phosphorus and aluminum expressed in molar ratios ranges from about 10:1 to 1:100, respectively, on an elemental basis. The zeolite is added to the aluminum phosphate hydrosol and the mixture is gelled. One method of gelling this mixture involves combining a gelling agent with the mixture and then dispersing the resultant combined into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The combined mixture preferably is dispersed into the oil bath in the form of droplets from a nozzle, orifice or rotating disk. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

Alternatively, the particles may be formed by spray-drying the mixture. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The amount of phosphorus-containing alumina component present (as the oxide) in the catalyst can range from about 10 to 70 mass-% and preferably from about 20 to 50 mass-%. The aluminum phosphate binder/matrix optionally may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

The aluminum-phosphate binder generally is amorphous, i.e., the binder material is essentially of amorphous character. Preferably less than about 10 mass-% of the binder pore volume is micropore volume, characteristic of crystalline material, and the micropore volume more preferably is less than 5% and optimally less than 2% of the pore volume. Crystalline aluminophosphate generally is an unsuitable binder material for preparing a strong, crush-resistant catalyst. Material that is not in an amorphous phase generally is present as gamma-alumina; as the phosphorus content of amorphous aluminum phosphate is decreased, therefore, the proportion of crystalline material is increased. The average bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 m$^2$/g, while spheroidal particles of aluminum phosphate may have surface areas of up to about 450 m$^2$/g. Al/P atomic ratios of the binder/matrix generally range from about 1/10 to 100/1, more typically from about 1/5 to 20/1, and often between about 1:1 and 5:1.

The catalyst may contain a metal component, preferably selected from components of the group consisting of gallium, rhenium and bismuth. Preferably, however, the catalyst consists essentially of a zeolitic aluminosilicate having a pore diameter from about 5 to 8 Å and an aluminum phosphate binder.

The zeolitic catalyst is subjected to selective pre-coking to increase the proportion of para-xylene in the para-xylene-rich product above equilibrium levels at disproportionation conditions. The proportion of para-xylene in the product above equilibrium levels at disproportionation conditions is generally at least about 80 mass-% and preferably about 90 mass-% or more of the $C_8$ aromatics. Pre-coking is effected on a fresh or regenerated catalyst, prior to its use for disproportionation, for a time ranging from about 0.5 hours to 10 days. The catalyst may be subjected to pre-coking either in-situ or ex-situ in order to increase the proportion of para-xylene in the $C_8$ aromatics product.

The pre-coking is effected at conditions relative to the subsequent disproportionation step comprising one or more of a higher temperature, lower pressure, higher space velocity. Such pre-coking conditions comprise a pressure of from about 100 kPa to 4 MPa absolute, and a liquid hourly space velocity of from about 0.2 to 20 $hr^{-1}$. The conditions comprise one or more of an inlet temperature at least about 50° C. higher; a pressure at least about 100 kPa lower, or preferably no more than about half of the pressure utilized in the subsequent disproportionation step. Lower pressure and/or a lower hydrogen/hydrocarbon ratio will lower the proportion of exothermic aromatic-saturation reactions, and thus restrict the temperature rise; the result thus should be a relatively flatter temperature profile. Thus a typical temperature range would be from about 300° to about 700° C. and a typical hydrogen to coke-forming feed range would be about 0.01 to about 5.

The use of nitrogen or another similarly inert diluent-gas such as methane, ethane, or propane is believed to be highly beneficial when included with hydrogen during the pre-coking phase. Such thermally inert diluent gas assists in controlling the temperature profile and is present in a molar ratio to coke-forming feed of about 0.01 to about 10, preferably in a ratio greater than 1. It is believed that the temperature profile affects the coking rate in various parts of the catalyst bed. A steep temperature gradient therefore will effect non-uniform coke deposition, and different parts of the catalyst bed thus will be selectivated to a different extent causing poorer performance in subsequent disproportionation reactions. Thus a typical temperature differential across the bed of catalyst during selective pre-coking would be between about a 10° C. increase or decrease, and preferably between about a 3° C. increase and about a 4° C. decrease.

Pre-coking effects a catalyst coke or carbon content of between about 5 and 40 mass-% carbon, and preferably between about 10 and 30 mass-% carbon. A coke-forming feed for pre-coking may comprise the feedstock to the disproportionation step as described hereinbelow, such as toluene, or other specific hydrocarbons or mixtures known in the art preferably comprising aromatics may be used. Further details relative to pre-coking are disclosed in U.S. Pat. No. 4,097,543 and U.S. Pat. No. 6,191,331, incorporated herein by reference.

The feedstock to the present process comprises alkylaromatic hydrocarbons of the general formula $C_6H_{(6-n)}R_n$, where n varies from 0 to 5 and R is $CH_3$, $C_2H_5$, $C_3H_7$, or $C_4H_9$, in any combination to obtain more valuable alkylaromatics. Suitable alkylaromatic hydrocarbons include, for example but without so limiting the invention, benzene, toluene, xylenes, ethylbenzene, trimethylbenzenes, ethyltoluenes, propylbenzenes, tetramethylbenzenes, ethyl-dimethylbenzenes, diethylbenzenes, methylpropylbenzenes, ethylpropylbenzenes, triethylbenzenes, di-isopropylbenzenes, and mixtures thereof.

The feedstock preferably comprises toluene, optionally in combination with $C_9$ aromatics, and suitably is derived from one or a variety of sources. Feedstocks may be produced synthetically, for example, from naphtha by catalytic reforming or by pyrolysis followed by hydrotreating to yield an aromatics-rich product. The feedstock may be derived from such product with suitable purity by extraction of aromatic hydrocarbons from a mixture of aromatic and nonaromatic hydrocarbons and fractionation of the extract. For instance, aromatics may be recovered from a reformate. The reformate may be produced by any of the processes known in the art. The aromatics then may be recovered from the reformate through the use of a selective solvent, such as one of the sulfolane type, in a liquid—liquid extraction zone. The recovered aromatics may then be separated into streams having the desired carbon number range by fractionation. The feedstock should contain no more than about 10 mass-% non-aromatics; the content of benzene and $C_8$ aromatics is principally an economic decision relating to the dilution of toluene from these aromatics. When the severity of reforming or pyrolysis is sufficiently high, extraction may be unnecessary and fractionation may be sufficient to prepare the feedstock.

Within the disproportionation process the feed usually is first heated by indirect heat exchange against the effluent of the reaction zone and is then further heated in a fired heater. The resulting vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both product and unconverted feed hydrocarbons. This effluent is normally cooled by indirect heat exchange against the stream entering the reaction zone and then further cooled through the use of air or cooling water. The temperature of the effluent stream generally is lowered by heat exchange sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream which is referred to herein as the disproportionation effluent stream is recovered as net stripper bottoms.

Conditions employed in the disproportionation process zone normally include a temperature of from about 200° to 600° C., and preferably from about 350° to about 575° C. The temperature required to maintain the desired degree of conversion will increase as the catalyst gradually loses activity during processing. Normal end-of-run temperatures may therefore exceed start-of-run temperatures by 65° C. or more.

The disproportionation zone is generally operated at hydrogen-to-hydrocarbon ranges about 0.1 to about 3.0, preferably less than about 1.0, and most preferably between about 0.2 to about 0.5. The ratio of hydrogen-to-hydrocarbon is calculated based on the molar ratio of free hydrogen compared against the feedstock hydrocarbon. Periodic increases in hydrogen-to-hydrocarbon above 0.5, and preferably in the range of 1 to 5 permit catalyst rejuvenation by hydrogenation of soft coke.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of para-xylene at the expense of conversion. Liquid hourly space velocity generally is in the range of from about 0.2 to 20 hr$^{-1}$.

The disproportionation effluent stream is separated into a light recycle stream, a para-xylene-rich mixed-$C_8$-aromatics product and a heavy-aromatics stream. The para-xylene-rich product may be sent to a xylene separation zone for recovery of pure para-xylene; optionally, other xylenes and ethylbenzene also may be recovered as pure products. The para-xylene-rich stream preferably contains para-xylene in proportion to total xylenes in excess of its equilibrium concentration at disproportionation conditions, more preferably at least 80 mass-% para-xylene, and most preferably at least about 85 mass-% para-xylene. The light recycle stream may be diverted to other uses such as to benzene and toluene recovery, but optionally a portion is recycled since it contains not only benzene and toluene but also amounts of non-aromatics which would remain with the benzene and reduce its commercial value. The heavy recycle stream contains substantially all of the $C_9$ and heavier aromatics and may be withdrawn as a product of the process.

The xylene-separation zone may utilize one or more different separation techniques such as fractionation, crystallization or selective adsorption to recover substantially pure para-xylene from the para-xylene-rich stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061, incorporated by reference. In an embodiment in which the para-xylene-rich product has a para-xylene content substantially in excess of the equilibrium concentration, recovery of para-xylene may be effected using only a single stage of crystallization corresponding to the higher-temperature purification stage of conventional crystallization.

An alternative separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may be obtained from U.S. Pat. No. 4,039,599 and U.S. Pat. No. 4,184,943. The xylene-separation zone may also incorporate a catalytic alkyl-aromatic isomerization zone within the separation loop, in order to shift the isomers of ortho- and meta-xylene towards para-xylene, as well as to isomerize ethyl benzene to xylene or else to dealkylate it to benzene. The benzene produced here may also be sent to the transalkylation zone. The xylene separation zone may also employ a simulated concurrent adsorptive separation process of U.S. Pat. No. 4,402,832. The extract and raffinate streams may be handled as described in these references or as described in U.S. Pat. No. 4,381,410 and U.S. Pat. No. 5,495,061.

Variations in the process combination described above are within the scope of the invention. For example, benzene as well as toluene may be charged to the disproportionation zone as a supplementary feedstock. The xylene-separation zone may use one or more of several known separation techniques such as adsorption, crystallization and fractionation. Ortho-xylene and/or meta-xylene may be recovered by one or more of such techniques as pure products from the xylene-separation zone.

The process of disproportionation may be carried out until the conversion of toluene is no longer economically favorable due to catalyst decline, deterioration, or deactivation. A typical economic target occurs when the initial conversion, as measured by temperature, has increased by 20° C. or more often 65° C. or greater, at which point the catalyst is rejuvenated by increasing the molar ratio of free hydrogen to feedstock hydrocarbons to greater than 0.5, preferably greater than 1.0. Accordingly, preferred rejuvenation conditions include free hydrogen present in a molar ratio to feedstock hydrocarbons of about 1 to about 5, an inlet temperature from about 200° to about 600° C., a pressure of from about 100 kPa to about 6 MPa absolute, and a liquid hourly space velocity of about 0.2 to about 20 hr$^{-1}$.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An alumina-phosphate-bound MFI catalyst was prepared to evaluate the invention. A first solution was prepared by adding phosphoric acid to an aqueous solution of hexamethylenetetraamine (HMT) in an amount to yield a phosphorus content of the finished catalyst equal to about 3.8 mass-% and an aluminum: phosphorus atomic ratio in the binder of about 1:1. A second solution was prepared by adding an MH-type zeolite having a Si/$Al_2$ ratio of about 39 to enough alumina sol, prepared by digesting metallic aluminum in hydrochloric acid, to yield a zeolite content in the finished catalyst equal to about 70 mass-%. These two solutions were commingled to achieve a homogeneous admixture of HMT, phosphorus, alumina sol, and zeolite. The admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This disproportionation catalyst was utilized in the pre-coking and disproportionation tests described hereinafter.

Example II

The catalyst was then pre-coked at conditions comprising a temperature of about 560° C., a pressure of 0.72 MPa and 4 weight hourly space velocity (WHSV) in the presence of a 0.5 hydrogen-to-hydrocarbon molar ratio for a period of time sufficient to effect approximately 90 mol-% para-xylene in total xylenes. Disproportionation of pure toluene then was carried out at 2.45 MPa and 4 WHSV in the presence of pure hydrogen at varying temperatures as required achieving a range of toluene conversion levels.

Figure 2:
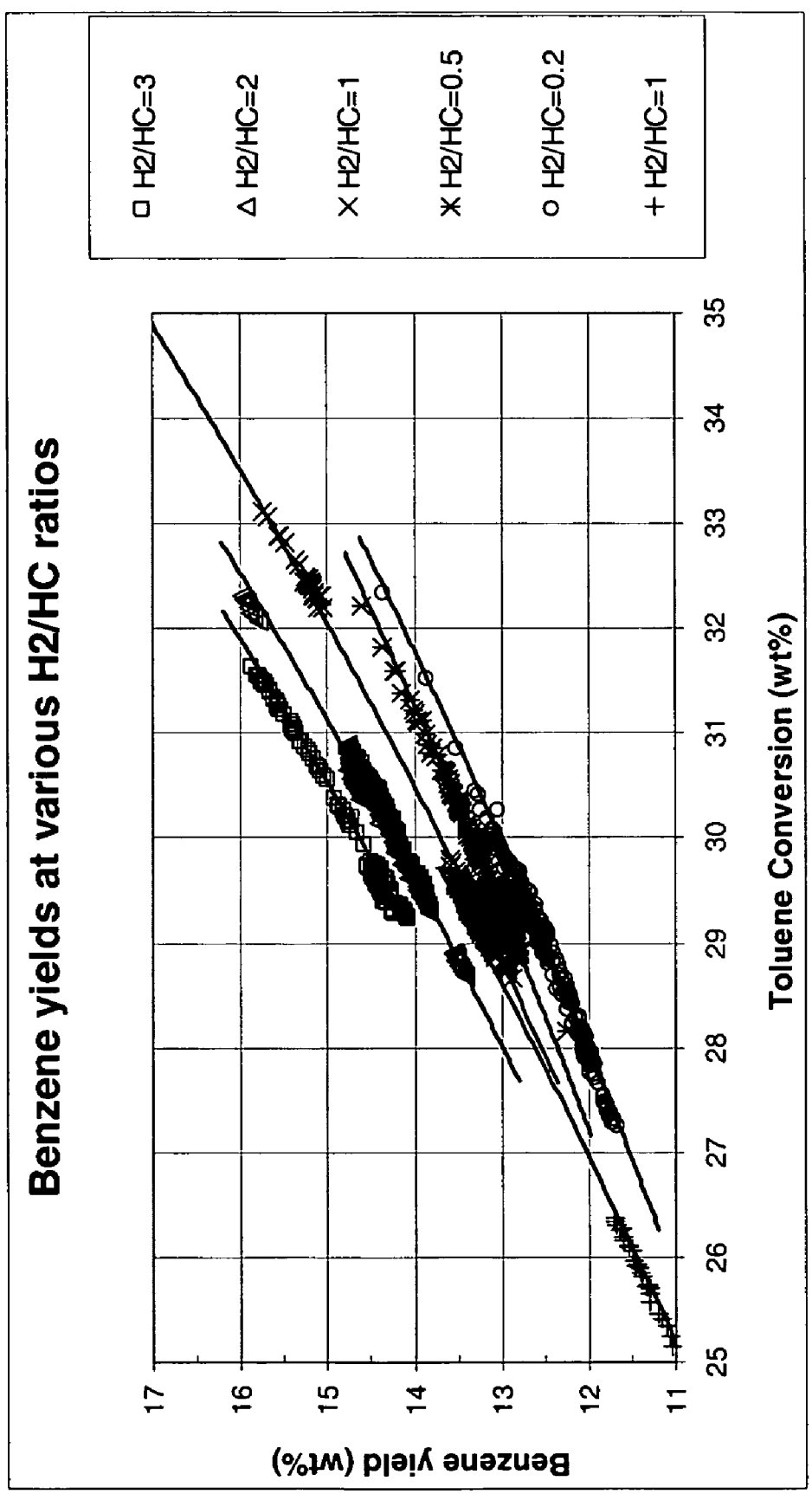
FIG. 2 shows the yields of benzene at various hydrogen-to-hydrocarbon ratios as toluene conversion increases over a selectively pre-coked catalyst.

Test-runs were conducted at hydrogen-to-hydrocarbon ratios 3.0, 2.0, 1.0, 0.5 and 0.2 in order to illustrate the invention. FIG. 1 shows the yields of para-xylene at these hydrogen-to-hydrocarbon ratios as toluene conversion increases over the selectively pre-coked catalyst. FIG. 2 shows the yields of benzene at these hydrogen-to-hydrocarbon ratios. Surprisingly, a critical maximum yield of para-xylene was found near a conversion level of 30 wt-%, and this maximum shifts to even higher conversion levels as the hydrogen-to-hydrocarbon ratio dropped below 3.0.

Following FIG. 1, the hydrogen-to-hydrocarbon ratio of 1.0 appears to provide a maximum yield of para-xylene in the range of 12.5 wt-% over a conversion level from about 30 to about 33 wt-%. Moreover, when the hydrogen-to-hydrocarbon ratio dropped below 1.0, the maximum shifts to an even higher conversion level. This conversion shift permits even greater yields of para-xylene to be achieved, which are unavailable at higher ratios of hydrogen-to-hydrocarbon.

Following FIG. 2, a benzene yield increase was observed as the conversion level of toluene increased in all cases. Yet, at every conversion level the yield of benzene decreases as the hydrogen-to-hydrocarbon ratio decreases. When the conversion level was less than about 33 wt-% with the hydrogen-to-hydrocarbon ratio less than 1.0, the benzene yield was lower than 15 wt-% in all cases.

Example III

The addition of nitrogen during the selectivation phase was investigated by conducting a first test without nitrogen and a test with a nitrogen-to-hydrocarbon ratio of 2.5 while maintaining a ratio of 0.5 hydrogen-to-hydrocarbons for both tests. Temperatures were maintained at 560° C., pressures at 0.72 MPa, and WHSV at 3 $hr^{-1}$. Disproportionation was subsequently carried out with pure toluene at 2.45 MPa, a WHSV of 4 $hr^{-1}$ and at a hydrogen-to-hydrocarbon ratio of 3.0 to achieve a toluene conversion of 30 wt-%.

Data obtained in the disproportionation test showed that at a ratio of para-xylene to total xylenes of 90 wt-%, the pure hydrogen selectivation procedure achieved a ration of benzene to total xylenes of about 1.6. However, the selectivation procedure using nitrogen achieved a ratio of benzene to total xylenes of about 1.3. Accordingly, the presence of an inert gas such as nitrogen during the selectivation procedure was confirmed to have a beneficial effect of reducing benzene production.

What is claimed is:

1. A process for the production of para-xylene comprising:
   a) disproportionating a toluene-containing feedstock by contacting the feedstock with a catalyst selectively pre-coked in the presence of an inert gas, said contacting occurring at disproportionation conditions comprising free hydrogen present in a molar ratio to feedstock hydrocarbons of about 0.1 to about 1.0, an inlet temperature from about 200° to about 600° C., a pressure of from about 100 kPa to about 6 MPa absolute, and a liquid hourly space velocity of about 0.2 to about 20 $hr^{-1}$ to obtain a para-xylene-rich product containing para-xylene in excess of its equilibrium concentration by conversion of greater than 30 wt-% of the toluene present in the feedstock;
   b) recovering para-xylene from the para-xylene-rich product by one or both of adsorption and crystallization; and
   c) carrying out step (a) for a period of time until the initial inlet temperature has increased by 20° C. or greater, at which point the catalyst is rejuvenated by increasing the molar ratio of free hydrogen to feedstock hydrocarbons to greater than 1.0.

2. The process of claim 1 wherein the conversion of toluene is about 33 wt-% or greater.

3. The process of claim 1 wherein the conversion of toluene is about 30 to about 33 wt-%.

4. The process of claim 3 wherein the para-xylene-rich product of step (b) further comprises benzene present in an amount no greater than about 15 wt-% calculated on a toluene feed basis.

5. The process of claim 1 wherein the rejuvenation conditions of step (d) further comprise free hydrogen present in a molar ratio to feedstock hydrocarbons of about 1 to about 5, an inlet temperature from about 200° to about 600° C., a pressure of from about 100 kPa to about 6 MPa absolute, and a liquid hourly space velocity of about 0.2 to about 20 $hr^{-1}$.

6. The process of claim 1 wherein the catalyst is selectively pre-coked by contacting a pentasil zeolite selected from the group consisting of MFI, MEL, MTW, and TON, with a coke-forming feed in the presence of a gas comprising hydrogen and an inert diluent-gas at pre-coking conditions comprising an inlet temperature of about 300° to about 700° C., a pressure of about 100 kPa to about 4 MPa absolute, a molar ratio of free hydrogen to coke-forming feed of about 0.1 to about 5, a molar ratio of inert diluent-gas to coke-forming feed of about 0.01 to about 10, and a liquid hourly space velocity of about 0.2 to about 20 $hr^{-1}$, to deposit between about 5 and about 40 mass-% carbon on the catalyst and obtain a selectively pre-coked catalyst.

7. The process of claim 6 wherein the inert diluent-gas is selected from the group consisting of nitrogen, methane, ethane, propane, and mixtures thereof.

* * * * *